(12) United States Patent
Hermansson et al.

(10) Patent No.: US 8,632,680 B2
(45) Date of Patent: Jan. 21, 2014

(54) COLUMN FOR LIQUID CHROMATOGRAPHY

(75) Inventors: Dan Hermansson, Uppsala (SE); Girish Kittur, Bangalore (IN); Patrik Akerstrom, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/575,064

(22) PCT Filed: Jan. 26, 2011

(86) PCT No.: PCT/SE2011/050079
§ 371 (c)(1),
(2), (4) Date: Jul. 25, 2010

(87) PCT Pub. No.: WO2011/093776
PCT Pub. Date: Aug. 4, 2011

(65) Prior Publication Data
US 2012/0292242 A1    Nov. 22, 2012

(30) Foreign Application Priority Data
Jan. 28, 2010    (IN) .......................................... 172/10

(51) Int. Cl.
*B01D 15/08*    (2006.01)
(52) U.S. Cl.
USPC ...................................... 210/198.2; 210/656

(58) Field of Classification Search
USPC ........... 210/635, 656, 659, 198.2, 456; 95/82; 96/101
See application file for complete search history.

(56) References Cited

U.S. PATENT DOCUMENTS

| | | | | |
|---|---|---|---|---|
| 3,228,646 | A | * | 1/1966 | Hinrichs .................... 248/354.3 |
| 4,865,728 | A | | 9/1989 | Larsson |
| 5,043,068 | A | * | 8/1991 | Karbachsch et al. ......... 210/350 |
| 5,378,361 | A | * | 1/1995 | Baeckstrum ............... 210/198.2 |
| 5,674,455 | A | | 10/1997 | Marchand et al. |
| 6,082,918 | A | * | 7/2000 | Gueret .......................... 401/126 |
| 6,139,732 | A | | 10/2000 | Pelletier |
| 2003/0173279 | A1 | * | 9/2003 | Aste ........................... 210/198.2 |
| 2005/0218048 | A1 | * | 10/2005 | Kato ............................. 210/130 |
| 2009/0230045 | A1 | * | 9/2009 | Kaneko et al. ............. 210/198.2 |
| 2010/0140174 | A1 | * | 6/2010 | Bailey et al. .................. 210/656 |
| 2010/0163490 | A1 | * | 7/2010 | Lasalle ......................... 210/656 |
| 2010/0193439 | A1 | * | 8/2010 | Yukon .......................... 210/656 |
| 2010/0206813 | A1 | * | 8/2010 | Yukon .......................... 210/656 |
| 2010/0230347 | A1 | * | 9/2010 | Haslem ........................ 210/523 |
| 2012/0031820 | A1 | * | 2/2012 | Reinhardt ....................... 210/85 |

* cited by examiner

*Primary Examiner* — Ernest G Therkorn

(57) ABSTRACT

Chromatography column comprising a column tube and at least one adjustable adapter assembly with a plunger that may be positioned at a plurality of longitudinal positions in the column tube, wherein the piston is arranged at the end of a threaded piston rod arranged with the threads engaged by a rotable end cap for enabling longitudinal movement of the piston by turning the end cap, and wherein the adaptor assembly comprises rotation prevention means arranged to prevent rotation of the plunger rod in response to turning of the end cap.

4 Claims, 5 Drawing Sheets

COLUMN FOR LIQUID CHROMATOGRAPHY

CROSS-REFERENCE TO RELATED APPLICATIONS

This application is a filing under 35 U.S.C. 371 of international application number PCT/SE2011/050079, filed Jan. 26, 2011, published on Aug. 4, 2011 as WO 2011/093776, which claims priority to application number 172/DEL/2010 filed in India on Jan. 28, 2010.

FIELD OF THE INVENTION

The present invention relates to a column for liquid chromatography, specifically a column capable of adjustable compression of separation medium contained therein, and to a method of packing separation medium in a chromatography column

BACKGROUND OF THE INVENTION

Liquid chromatography is a process by which one or more compounds from a chemical mixture may be separated and identified. In order for a chromatographic column to be able to separate biological substances effectively, it is usual to pack fine particles of separation material as tightly and as uniformly as possible in the column tube Filling of the column, or column packing as it is often referred to, is normally effected by closing one end of the column with an outlet means which includes a filter element, and pumping a liquid suspension of the particles under pressure into the other end of the column. Whereas the pumped liquid is able to pass through the filter element essentially unobstructed, the particles are retained by the filter element, so as to build up a particle bed along the length of the tube. As the column tube is filled, the particles are pressed out towards the wall of the tube and the particle bed obtains a stable compaction state with the particles well distributed, this state being maintained during the whole of the filling process.

However, when the column tube has been filled with particles and pumping of the liquid suspension is terminated to enable an inlet element to be fitted to the filling-end of the tube, the stable restraining force in the particle bed is partially lost, resulting in expansion of the particle bed. Consequently, when the column tube is once again placed under pressure, disturbing heterogeneities or irregularities are liable to occur in the particle bed, such as the formation of channels and dead volumes.

The uniformity of the packing medium within the column has a significant effect on column performance. It is desired that the particles comprising the packing medium be perfectly arranged and completely homogeneous so that the transport liquid and the sample mixture move at uniform rates through the column Areas of loose packing medium create channels causing locally increased flow rates while areas that are partially plugged due to particle aggregation create eddies that retard the flow. Such local variations in the flow rate caused by non-uniform packing medium result in transport liquid mixing that degrades the column performance resulting in broadening of the peaks and a concomitant decrease the resolving capability of the chromatography apparatus.

In order to provide versatile columns, there is provided a range of columns capable of adjustable compression of separation medium contained therein. Such columns typically comprise one or two plungers that are moveable in the column tube in order to adjust the column length. Examples of prior art columns include the XK column series from GE Healthcare, and the Kronlab ECOplus columns from YMC Europe GMBH.

SUMMARY OF THE INVENTION

The object of the invention is to provide a new column for liquid chromatography and a method of packing a chromatography column, which overcomes one or more drawbacks of the prior art. This is achieved by the column for liquid chromatography and the method of packing a chromatography column as defined in the independent claim.

One advantage with such a column for liquid chromatography is that it is.

Another advantage is that Further scope of applicability of the present invention will become apparent from the detailed description given hereinafter. However, it should be understood that the detailed description and specific examples while indicating preferred embodiments of the invention are given by way of illustration only. Various changes and modifications within the spirit and scope of the invention will become apparent to those skilled in the art from the detailed description below.

BRIEF DESCRIPTION OF DRAWINGS

These and other advantages of the present invention will become more apparent as the following description is read in conjunction with the accompanying drawings, wherein.

DETAILED DESCRIPTION OF THE PREFERRED EMBODIMENTS

The presently preferred embodiments of the invention are described with reference to the drawings, where like components are identified with the same numerals. The descriptions of the preferred embodiments are exemplary and are not intended to limit the scope of the invention.

Figure 1:
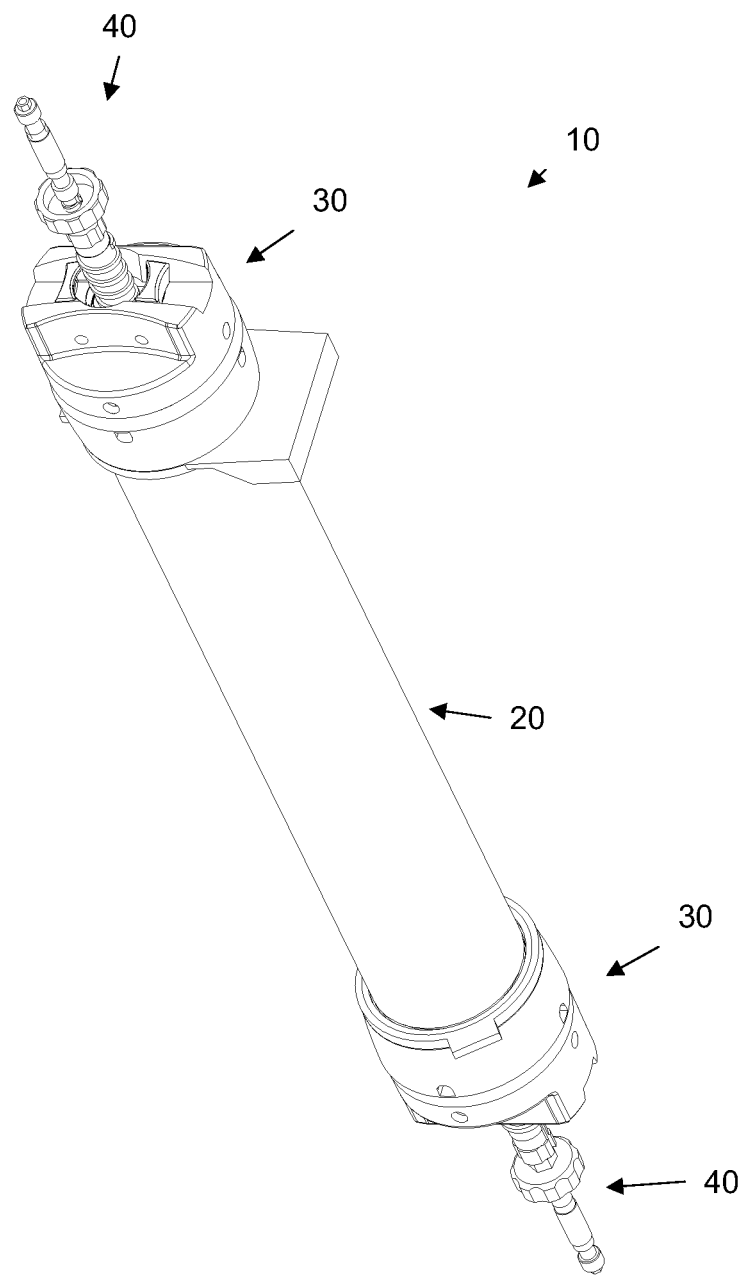
FIG. 1 shows a column for liquid chromatography in accordance with an embodiment of the invention.

FIG. 1 shows a column 10 for liquid chromatography in accordance with an embodiment of the invention. The column 10 comprises a column tube 20 and two adapters 30 with tubing 40 at each end for connection to valves, pumps or monitors (not shown).

Figure 2:
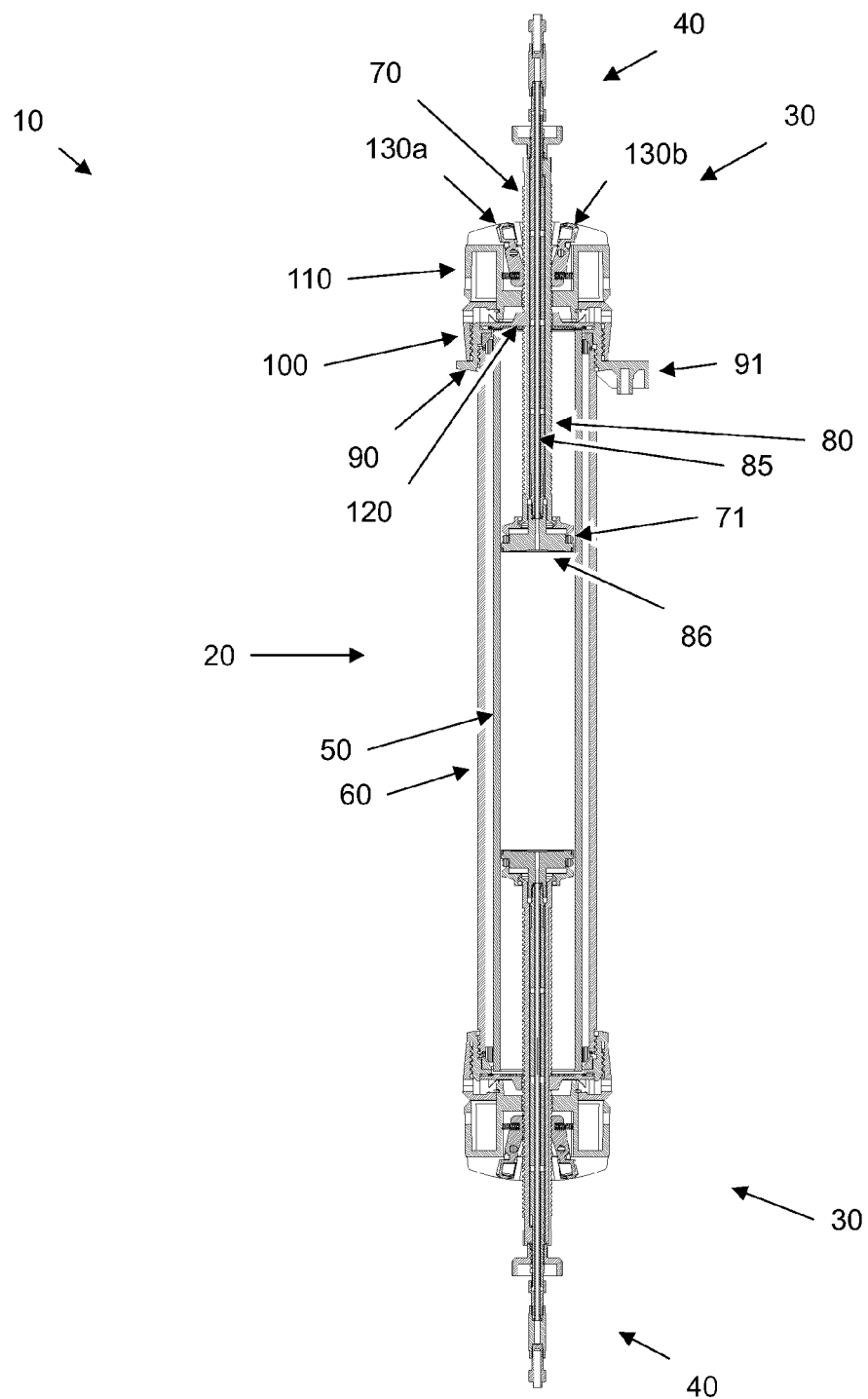
FIG. 2 shows the column of FIG. 1 in cross-section.
Figure 3:
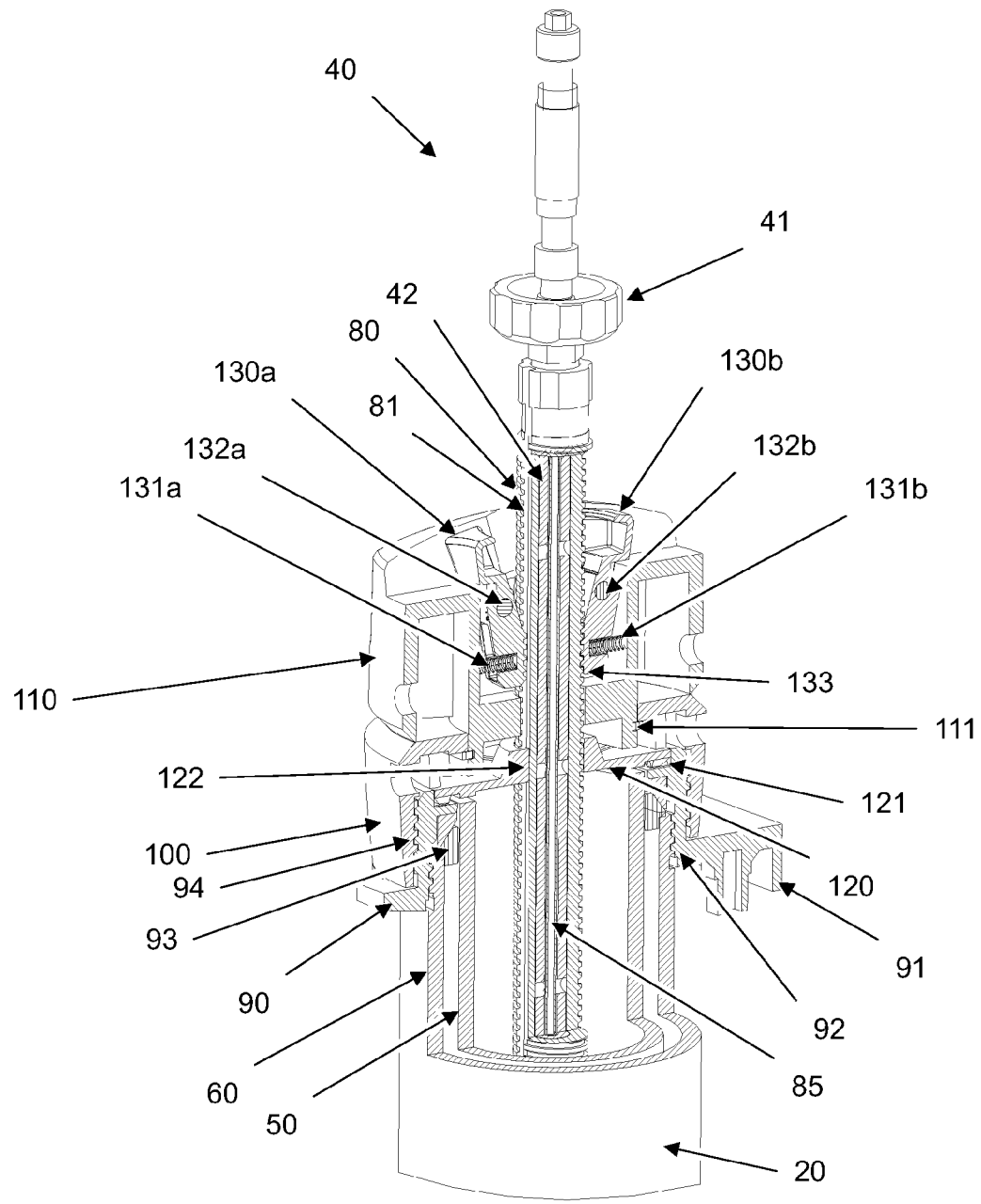
FIG. 3 is a partial cross-sectional view of one end of the column of FIG. 1.
Figure 4:
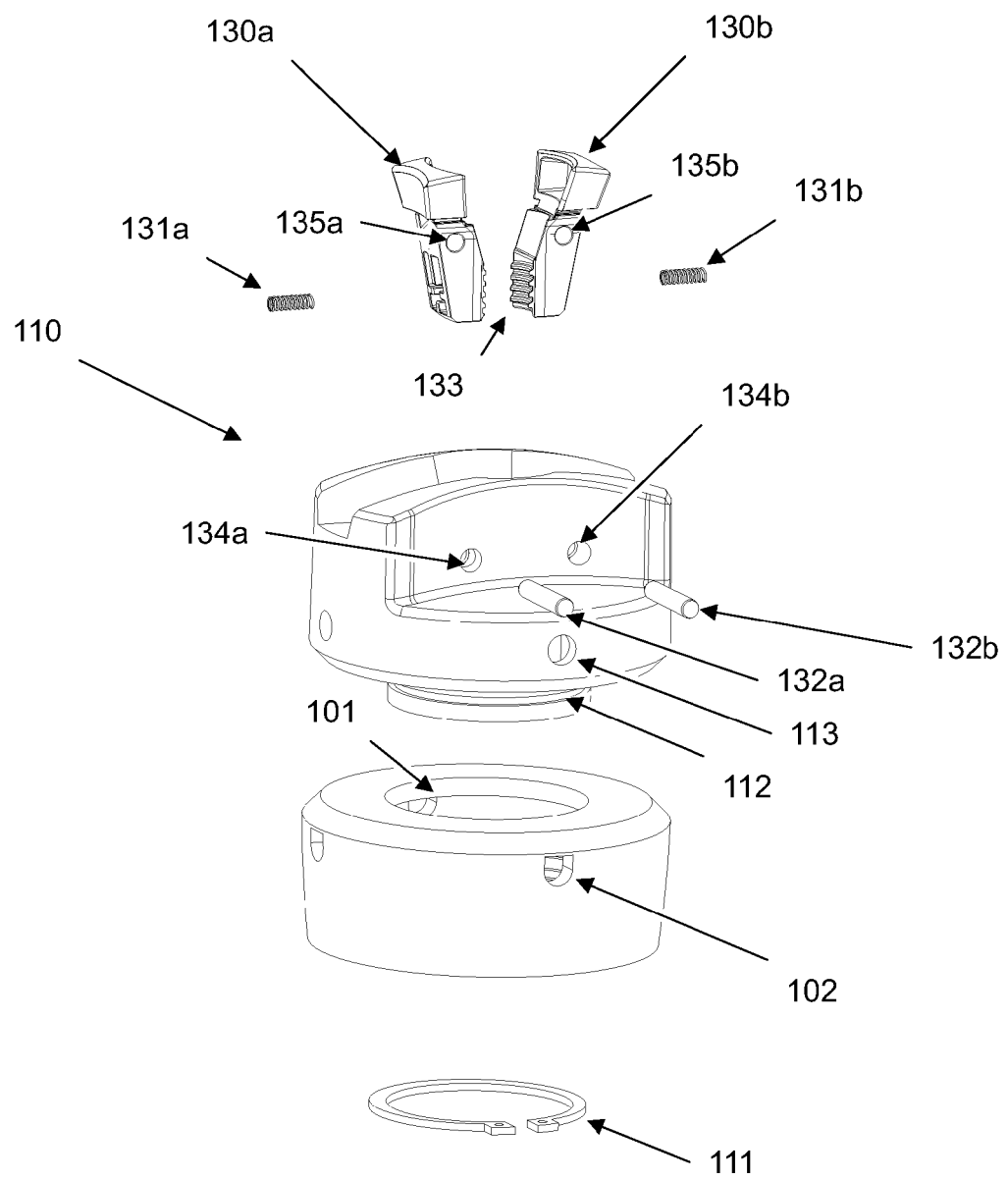
FIG. 4 is a partial exploded view of an end piece assembly.

FIG. 2 shows the column of FIG. 1 in cross section. In the disclosed embodiment, the adapters 30 are essentially identical and are both of "plunger-type" with a plunger 70 allowing adjustment of the bed height from both ends. FIG. 3 is an enlarged view of an adaptor assembly 30 and one end of the column tubing assembly 50, and FIG. 4 is an exploded view of the end cap 110 and the end sleeve 100. As the columns are equipped with two such adapters 30, a large range of bed heights between the plungers 70 can be obtained. The column further comprises a column tube 50 comprised of a material that is inert to the solvents and samples that may be run through the column, such as glass, stainless steel or the like. The column tube 50 may be of any suitable diameter, depending on the desired column capacity and in one embodiment it is coaxially surrounded by a protection tube 60 which acts as a safety barrier in case of failure of the column tube 50 if it accidentally should be exposed to too high pressure and break. The column tube 50 and the protection tube 60 ate interconnected at each end by a tubing end piece 90 arranged to hold the column tube 50 and protection tube 60 in position with respect to each other. The tubing end pieces 90 further provides sealed connection interfaces for the adaptors 30 to the column tube 50. In the disclosed embodiment, the tubing end pieces 90 are firmly attached to the protection tube 60 by threads 92, and the column tube 50 is held in position by a compression seal 93. In other embodiments, the protection tube 60 may be omitted and the tubing end piece 90 or the adaptor 30 may be attached directly on the column tube 50. In the disclosed embodiment, the upper tubing end piece 90 is provided with a column holder section 91 arranged to facilitate holding of the column assembly 10.

The adapter 30 comprises an end sleeve 100, an end cap 110 and a plunger assembly 70 with an anti-rotator plate 120. The end sleeve 100 is arranged to be firmly attached to the tubing end piece 90 by threads 94 and to fixate an anti rotation plate 120 in a fixed position there between. The end cap 110 is rotably attached to the end sleeve 100 by a retaining ring 111 and it comprises a central through hole for receiving the plunger assembly 70. The plunger assembly 70 comprises an elongated threaded plunger rod 80 for applying packing force on the bed. The end cap 110 comprises spring loaded release buttons 130*a* and 130*b* with threaded lock surfaces 133 that are formed to mate the threads of the plunger rod 80 to allow adjustment of the position of the plunger assembly 70 with respect to the end sleeve 100 by turning the end cap 110. Alternatively, the position of the plunger assembly 70 can be adjusted by pressing the release buttons to disengage the lock surfaces 133 from the plunger rod 80, whereby the plunger assembly can be moved manually up or down. Manual movement of the plunger assembly 70 allows quick positioning of the plunger assembly 70 to set the desired bed height, whereas the end cap 110 may be used for fine adjustment of the bed height and for subsequent compression of the bed. The release buttons 130*a* and 130*b* are pivotally linked to the end cap 110 by button pins 132*a* and 132*b* arranged in through holes 134*a* and 134*b* in the end cap 110 and which pins 132*a* and 132*b* extends through button holes 135*a* and 135*b*, respectively. The release buttons 130*a* and 130*b* are forced in the engaging direction by button springs 131*a* and 131*b*. In order to allow efficient manual movement of the plunger rod 80 with respect to the release buttons 130*a* and 130*b*, their mating threading is asymmetric with respect to the axis of movement of the plunger rod 80, in that the threading is tapered in the compression direction when the plunger assembly is moved into the column tube 50 to allow compression without need to press the release buttons 130*a* and 130*b* as the tapered threading automatically disengages them from the plunger rod 80. With respect to the counter-compression direction, the mating threading of the release buttons 130*a* and 130*b*, and the plunger rod 80 is essentially transverse to provide a stiff lock. Moreover, the pivot axis of each release button 130*a* and 130*b* is arranged prior to the lock surface 133 in the compression direction of the plunger assembly 70, whereby a force on the plunger rod 80 in the counter-compression direction effectively will tighten the interaction of the threading due to a lever action of the release buttons 130*a* and 130*b*.

Figure 5:
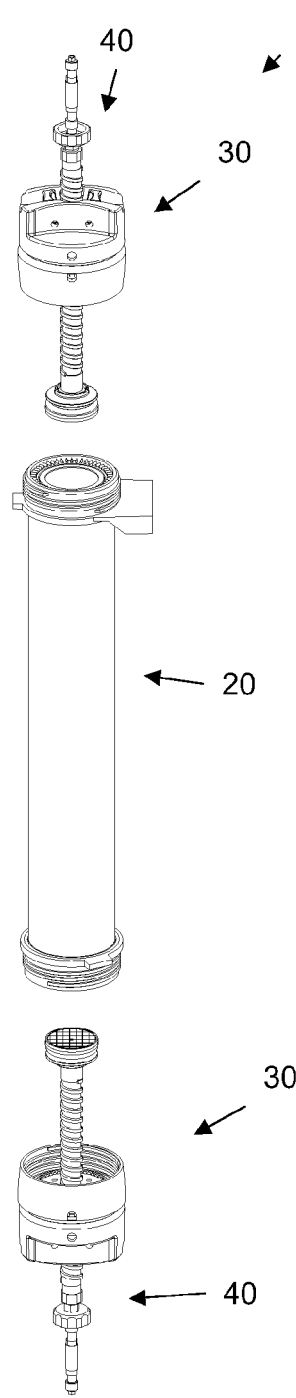
FIG. 5 is a disassembled column of FIG. 1.

The plunger assembly 70 comprises a plunger 86 arranged to keep the bed in a compressed state and to distribute the sample fluid over the full diameter of the bed. The plunger is provided with a fine mesh net or the like to avoid bed particles from entering the fluid paths. The plunger 86 is in fluidic contact with a chromatography system (not shown) through tubing 85 arranged in the plunger rod 80. In the disclosed embodiment, the plunger is provided with an adjustable seal 71 against the wall of the column tube 50, disclosed more in detail with reference to FIG. 6 below. As is mentioned above, the plunger assembly 70 may further be moved in the compression and counter-compression directions by turning the end cap 110 with respect to the end sleeve 100. In order to avoid distortion of the bed at the interface to the plunger the end sleeve 100 is provided with an anti-rotation member 120 comprising a protrusion 122 arranged to interact with a longitudinal groove 81 in the plunger rod 80 to prevent it from rotating with respect to the column tube 50 when turning the end cap 110 to move the plunger rod 80 in the longitudinal direction. In the disclosed embodiment, the anti rotation member 122 is provided with one protrusion 122, but in other embodiments, it may be provided with two or more protrusions, and the plunger rod 80 with a corresponding number of longitudinal grooves 81. In the disclosed embodiment, the anti rotation member 122 is provided as a separate member that is arranged in between the end sleeve 100 and the end piece 90, and wherein the anti rotation member 122 is provided with a rotation lock structure 121 arranged to prevent rotation of the same, when it is pressed against the end piece 90, while allowing the end sleeve 100 to be tightly attached to the end piece by threads 94. In the disclosed embodiment the rotation lock structure 121 is comprised of an annular teeth structure on the surface facing the end piece 90, and wherein the corresponding surface of the end piece 90 is provided with a mating teeth structure. According to one embodiment, the anti rotation member 122 may be formed as an integral part of the end sleeve 100. FIG. 5 shows the column 10 with the adapters 30 removed from the column tube 20, wherein the teeth structure of the end piece 90 is exposed.

Figure 6:
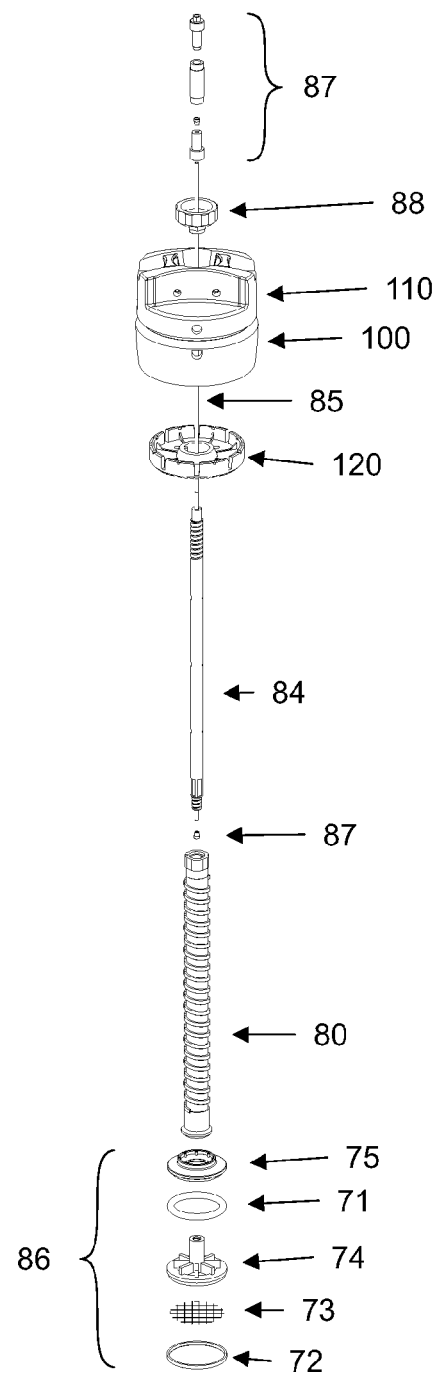
FIG. 6 is an exploded view of an adaptor assembly of the column of FIG. 1.

FIG. 6 shows an exploded view of one adapter 30 wherein the anti-rotation member 120 is shown separately. Starting from the bottom, the plunger 86 is comprised of a mesh retaining ring 72, a mesh 73, a plunger distributor body 74, a seal 71 in the form of an o-ring, and a plunger seal compression body 75. The plunger compression body is attached to and supported by the plunger rod 80, whereas the plunger distribution body is attached to a plunger sealing rod 84 and to fluidics tubing 85. Above the end cap 110 the plunger sealing rod 84 is attached to a plunger sealing knob 88 by means of threads. In the assembled state the sealing knob 88 abuts the upper end of the plunger rod 80, and when it is rotated in the sealing direction it moves the plunger sealing rod 84 and thus the plunger distribution body 74 upwards with respect to the plunger rod 80 and the plunger seal compression body 75, whereby the seal 71 is pressed against the inner wall of the column tube 50 to achieve a tight seal there between. The upper end of the fluidics tubing is attached to suitable fluidics fittings 87 to be connected to a chromatography system.

Mode of Usage:

A. Inserting and adjusting the adapter used as bottom end piece:
   1. Insert the bottom adapter 30 in the column tube 50, tighten the end sleeve 100 to the end piece 90, and adjust the plunger 86 to the desired level.
   2. Tighten the seling knob 88 to seal the sealing O-ring 71 against the column tube wall 50.

B. Packing the column:
   1. Remove the top adapter 30 and make sure the plunger 86 of the bottom adapter 30 is in the right place with the O-ring 71 tightened.

2. Pour a small amount of packing liquid into the column tube 50 and let it drain until the level of liquid in the tube is 2 to 3 mm above the plunger 86.
3. Close the column outlet on the bottom adapter 30 e.g. using a stop plug.
4. Carefully fill chromatography medium into the column tube 50 avoiding introducing air bubbles.
5. Slacken the sealing O-ring 71 of the top adapter 30 and insert the plunger 86 in the column tube at an angle so that no air is trapped under the plunger 86.
6. Fasten the adapter to the column tube 50 by turning the end sleeve 100 down.
7. Tighten the sealing knob 88 to seal the sealing O-ring 71 against the column wall 50.
8. Slide the plunger 86 slowly down by turning the end cap 110 so that air in the plunger 86 and capillary tubing 85 is displaced by the eluent.
9. Pack the column 10 according to appropriate media instruction.

According to one embodiment, there of the packing may comprise one or more of the following steps:

1. Flowing packing fluid through the column at a predetermined rate, such as 750 cm/h.
2. Consolidating the bed during a predetermined time period, such as 5 min
3. Registering the top of the thus compressed bed.
4. Terminating the flow of packing liquid
5. Positioning the plunger 86 at a predetermined distance, e.g. 10 mm, above the bed surface, to make sure that the bed surface is not disturbed.
6. Tightening the sealing knob 88 to seal the o-ring seal 71 on the plunger 86 and start turning the end cap 110 until the plunger reach the top of the compressed bed as registered.
7. Measuring the bed height and calculate the desired bed height by dividing the measured bed height with the predetermined packing factor.
8. Turn the end cap 110 until the desired bed height is reached.

B. Adjusting the piston 86 position using release buttons 130*a* and 130*b*. To readjust the position of the piston in the column:

1. Loosen the sealing knob 88 of the top adapter 30 to slacken the seal O-ring 71.
2. Press in the release buttons 130*a* and 130*b* and adjust the piston 86 to a position just above the bed level.
3. Tighten the sealing knob 88 to obtain a good seal.
4. Adjust the piston position by turning the end cap 100.
5. Turning of the end cap 100 can also be used for axial compression of the gel bed as described in the media instruction. If needed, a spanner may be used to turn the end cap 100.

Although the present invention has been described and illustrated in detail, it is to be clearly understood that this is done by way of illustration and example only and is not to be taken by way of limitation. The scope is to be limited only by the terms of the appended claims.

What is claimed is:

1. A chromatography column comprising a column tube with at least one tubing end piece, and at least one adjustable adapter assembly with an end sleeve attached to the tubing end piece by a thread arrangement, an end cap rotably attached to the end sleeve, and a plunger assembly with a plunger arranged at the end of a threaded plunger rod arranged with the threads engaged by said rotable end cap for enabling longitudinal movement of the plunger by turning the end cap, wherein the plunger rod comprises a longitudinal groove and the adaptor assembly comprises an anti-rotation plate with a protrusion that engages the longitudinal groove to prevent rotation of the plunger, wherein the anti-rotation plate is arranged in between the end sleeve and the tubing end piece, and wherein the anti-rotation plate is provided with a rotation lock structure arranged to prevent rotation of the same with respect to the tubing end piece.

2. The chromatography column of claim 1, wherein the end cap comprises spring loaded release buttons with threaded lock surfaces that are formed to releasably mate the threads of the plunger rod.

3. The chromatography column of claim 2, wherein the threads of the release buttons and the plunger rod are tapered in the compression direction of the plunger rod and essentially transverse in the counter-compression direction.

4. The chromatography column of claim 1, wherein the rotation lock structure is comprised of an annular teeth structure on the surface facing the end piece, and wherein the corresponding surface of the end piece is provided with a mating teeth structure.

* * * * *